(12) United States Patent
Iftikhar et al.

(10) Patent No.: US 10,575,622 B2
(45) Date of Patent: Mar. 3, 2020

(54) MODELLING SYSTEM

(71) Applicant: Conopco, Inc., Englewood Cliffs, NJ (US)

(72) Inventors: Abid Iftikhar, Liverpool (GB); Robert McKeown, Flintshire (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/080,825

(22) PCT Filed: Mar. 2, 2017

(86) PCT No.: PCT/EP2017/054962
§ 371 (c)(1),
(2) Date: Aug. 29, 2018

(87) PCT Pub. No.: WO2017/153260
PCT Pub. Date: Sep. 14, 2017

(65) Prior Publication Data
US 2019/0059559 A1 Feb. 28, 2019

(30) Foreign Application Priority Data
Mar. 9, 2016 (EP) .................................. 16159407

(51) Int. Cl.
*A45D 44/00* (2006.01)
*A61B 5/107* (2006.01)
(Continued)

(52) U.S. Cl.
CPC ............ *A45D 44/00* (2013.01); *A61B 5/1077* (2013.01); *A61B 5/1079* (2013.01); *A61B 5/448* (2013.01);
(Continued)

(58) Field of Classification Search
None
See application file for complete search history.

(56) References Cited

FOREIGN PATENT DOCUMENTS

WO  WO2014041186  3/2014

OTHER PUBLICATIONS

Ribeiro et al "Potential of human γD-crystallin for hair damage repair: insights into the mechanical properties and biocompatibility", International Journal of Cosmetic Science, 2013, 35, 458-466. (Year: 2013).*

(Continued)

*Primary Examiner* — Kee M Tung
*Assistant Examiner* — Patrick F Valdez
(74) *Attorney, Agent, or Firm* — Foley & Lardner LLP

(57) ABSTRACT

A method of analysing at least one hair surface using a 3D printer includes collecting a first imaging data for the at least one hair surface; applying at least one assault to the at least one hair surface; collecting a second imaging data for the at least one hair surface after applying the at least one assault; converting the first imaging data into a first formatted data, the first formatted data associated with the 3D printer; converting the second imaging data into a second formatted data, the second formatted data associated with the 3D printer; producing a first 3D model of the at least one hair surface from the 3D printer using the first formatted data; and producing a second 3D model of the at least one hair surface from the 3D printer using the second formatted data.

10 Claims, 2 Drawing Sheets

(51) Int. Cl.
- G01N 33/68 (2006.01)
- A61B 5/00 (2006.01)
- B33Y 50/02 (2015.01)
- B29C 64/386 (2017.01)
- G06T 17/00 (2006.01)

(52) U.S. Cl.
CPC ............ *B29C 64/386* (2017.08); *B33Y 50/02* (2014.12); *G01N 33/68* (2013.01); *G06T 17/00* (2013.01); *A45D 2044/007* (2013.01); *G01N 2333/4742* (2013.01); *G01N 2500/00* (2013.01)

(56) References Cited

OTHER PUBLICATIONS

Lee et al "Accuracy of three-dimensional printing for manufacturing replica teeth", The Korean Journal of Orthodontics, 217-225, 2015. (Year: 2015).*

Ou et al "Cilllia—3D Printed Micro-Pillar Structures for Surface Texture, Actuation and Sensing", CHI'16, May 7-12, 2016. (Year: 2016).*

Hyung Jin Ahn et al.; An ultrastuctural study of hair fiber damage and restoration following treatment with permanent hair dye; International Journal of Dermatology; Feb. 1, 2002; pp. 88-92; XP055270760; vol. 41 No. 2.

Search Report and Written Opinion in PCTEP2017054962; dated Mar. 27, 2017.

Monteiro et al.; Morphological Analysis of Polymers on Hair Fibers by SEM and AFM; Materials Research; Dec. 1, 2003; pp. 501-506; XP055270758; vol. 6 No. 4.

Gierad Laput et al.; 3D Printed Hair: Fused Deposition Modeling of Soft strands, Fiberts and Bristles; User Interface Software and Technology; Jan. 1, 2015; pp. 593-597; XP055270761.

Gould et al.; Electron-microscopy-image analysis: Quantification of ultrastructural changes in hair fiber cross sections as a result of cosmetic treatment presented at the Society of Cosmetic Chemists Annual Meeting; Journal of the Society of Cosmetic Chemists; Jan. 1, 1985; pp. 53-59; XP055270759; vol. 36.

Search Report and Written Opinion in EP16159407; dated May 12, 2016; European Patent Office (EPO).

Search Report and Written Opinion in EP16159406; dated May 12, 2016.

Search Report and Written Opinion in PCTEP2017054969; dated Mar. 24, 2017.

* cited by examiner

converted into the collected database via a 3D printer. The printer prints the collected data as 3D formatted objects to be presented to consumers. This allows for further understanding, in particular in educational tools, in communication with the press and media, in professional environments and at point of sale.

MODELLING SYSTEM

CROSS-REFERENCE TO RELATED APPLICATIONS

This application claims priority to International Patent Application No. PCT/EP2017/054962, filed on Mar. 2, 2017, and European Patent Application No. 16159407.2, filed on Mar. 9, 2016, both of which are incorporated herein by reference in their entireties.

FIELD OF THE INVENTION

The present invention relates to a method of analysing the effect of assaults, such as environmental conditions, mechanical assaults, chemical treatments, and every day hair care regimes on hair, and to a method of determining and applying a suitable treatment to the hair, using 3D images.

BACKGROUND

HYUNG JIN AHN ET AL: "An ultrastructural study of hair fiber damage and restoration following treatment with permanent hair dye", INTERNATIONAL JOURNAL OF DERMATOLOGY, vol. 41, no. 2, 1 Feb. 2002 (2002-02-01), pages 88-92, XP055270760, UK; discloses an ultra-structural study of hair fibre damage and restoration using electron microscopy.

VALERIA FERNANDES MONTEIRO ET AL: "Morphological analysis of polymers on hair fibers by SEM and AFM", MATERIALS RESEARCH, vol. 6, no. 4, 1 Dec. 2003 (2003-12-01), pages 501-506, XP055270758, BR; and JACALYN G GOULD ET AL: "Electron microscopy-image analysis: Quantification of ultrastructural changes in hair fiber cross sections as a result of cosmetic treatment; Presented at the Society of Cosmetic Chemists Annual Meeting", J. SOC. COSMET. CHEM, vol. 36, 1 Jan. 1985 (1985-01-01), pages 53-59, XP055270759 disclose imaging and microscope-based approaches for analysing the effect of treatments on hair fibres.

GIERAD LAPUT ET AL: "3D Printed Hair: Fused Deposition Modelling of Soft Strands, Fibers and Bristles", USER INTERFACE SOFTWARE AND TECHNOLOGY, 1 Jan. 2015, (2015-01-01), pages 593-597, XP055270761, discloses the production of hair fibres by 3D printing.

WO14041186A1 describes a system or component such as software for 3D modelling of bodies.

Consumers are aware of the damage that certain assaults such as treatments, protocols and hair care regimes can cause to the surface and structure of their hair. Although remedial treatments are available to mitigate these detrimental effects, the concept can be difficult for the consumer to grasp and the full effects of the remedial treatments difficult to fully comprehend.

Despite the prior art, there remains a need for new and improved methods of determining effects of treatments and assaults on hair.

The method of the invention can be used to assess properties of hair fibres, which have been exposed to various treatments and assaults.

SUMMARY

In a first aspect, the present invention provides a method of analysing the effect of an assault on hair, comprising the steps of:
(i) collecting imaging data for at least one hair surface,
(ii) applying at least one assault to the at least one hair surface,
(iii) collecting imaging data for the at least one hair surface arising from step (ii),
(iv) converting the imaging data collected at steps (i) and (iii) into a format suitable to create magnified images from a 3D printer,
(v) producing magnified 3D models of the at least one hair surface from a 3D printer using the data from step iv,
(vi) comparing the 3D model arising from step (iii) to the 3D model of step (i) and
(vii) assessing the degree of damage to the hair.

Preferably, steps (ii) to (vii) are repeated. Steps (ii) to (vii) may be repeated multiple times in order to assess the impact of repeated or long term exposure to the assault. For example, from 2 to 20 times, preferably from 2 to 8 times.

This method allows the properties shown in the magnified image/3D model at step (v) of the method of the invention to be compared to the initial image/3D model from step (i).

Properties that may be seen in the magnified image are external topographical aspects of the hair fibre, for example, cuticle lift, cuticle damage (for example, chipping, splitting, change in shape and breaking), cuticle erosion, split ends, kinks, blobs, cracks, holes and knots. These may be present at the initial imaging stage (i) depending on the age and condition of the hair at the beginning of the method. Thus, it is possible to illustrate to the consumer the impact of their usual hair regime and of other everyday assaults suffered by their hair.

The image may be used to assess the degree of damage to the hair, preferably by comparison to a scale. Preferably, the scale comprises indicators, for example numbers or letters, where the indicators correspond to incremental levels of damage. In another preferred embodiment, the scale of damage comprises illustrations, such as photographs or CAD images that illustrate the degree of damage in increments. Both indicators and illustrations may be used together.

A preferred method comprises the steps of:
(i) collecting imaging data for at least one hair surface,
(ii) applying at least one assault to the at least one hair surface,
(iii) collecting imaging data for the at least one hair surface arising from step (ii),
(iv) converting the imaging data collected at steps (i) and (iii) into a format suitable to create magnified images from a 3D printer,
(v) producing magnified 3D models of the at least one hair surface from a 3D printer using the data from step iv,
(vi) comparing the 3D model arising from step (iii) to the 3D model arising from step (i),
(vii) assessing the degree of damage to the hair, and
(viii) repeating steps (ii) to (vii).

The method of the invention can be used to define the hair need of an individual.

The method of the invention may be used in an educational tool, in communication with press, media or trade, at point of sale, in professional environments such as salons, and in commercial material, advertisement material and promotional material.

In a second aspect of the invention, there is provided a method of determining the effect of a beneficial treatment or regime on hair. The method comprises a step of applying a suitable beneficial treatment or regime to the hair, where the treatment is determined according to the analysis of the 3D images. Implementation of a beneficial treatment, or beneficial changes to the treatment that the individual is using are envisaged within the method of the invention. For example, treatments that are suitable for the properties revealed in the magnified 3D image, such as treatments for lifted cuticles, or for eroded cuticles (as is apparent in bleached hair), or for split ends and so on. The treatment may also be determined according to the assessment of the degree of damage to the hair; or by a combination of both the analysis of the 3D images and the assessment of the degree of damage. Beneficial regimes include making changes to a current regime such as switching from blow drying to natural drying, switching to hair colourant treatments that have a lower peroxide content than current, reducing combing to reduce further damage to damaged cuticles, washing hair less frequently, and so on. The implementation of a new beneficial regime, such as a regular use of a repair treatment, is also envisaged.

The method of the second aspect of the invention comprises the steps of:
 (i) collecting imaging data for at least one hair surface,
 (ii) converting the imaging data from step (i) and optional step (ii) into a format suitable to create magnified images from a 3D printer,
 (iii) producing magnified 3D model(s) of the at least one hair surface using the data from step (iii),
 (iv) analyzing the properties of the hair surface apparent from the 3D model(s),
 (v) assessing the degree of damage to the hair,
 (vi) applying a suitable beneficial treatment or regime to the hair, taking into account the findings of steps (v) and/or (vi),
 (vii) collecting imaging data for the at least one hair surface arising from step (vii) and producing a magnified 3D model of the treated hair surface using the imaging data,
 (viii) comparing the 3D model arising from step (viii) to the 3D model arising from step (i) or step (ii), and
 (ix) assessing the beneficial effect to the hair.

In this way it is possible to demonstrate any surface improvement, such as "smoothing", arising from the application of the treatment or regimes to the hair.

Steps (vi) to (ix) may be repeated.

In this method, at least one assault may be applied to the at least one hair surface and collecting imaging data for the resulting hair surface, after step (i).

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

DETAILED DESCRIPTION

The Assault

Figure 1:
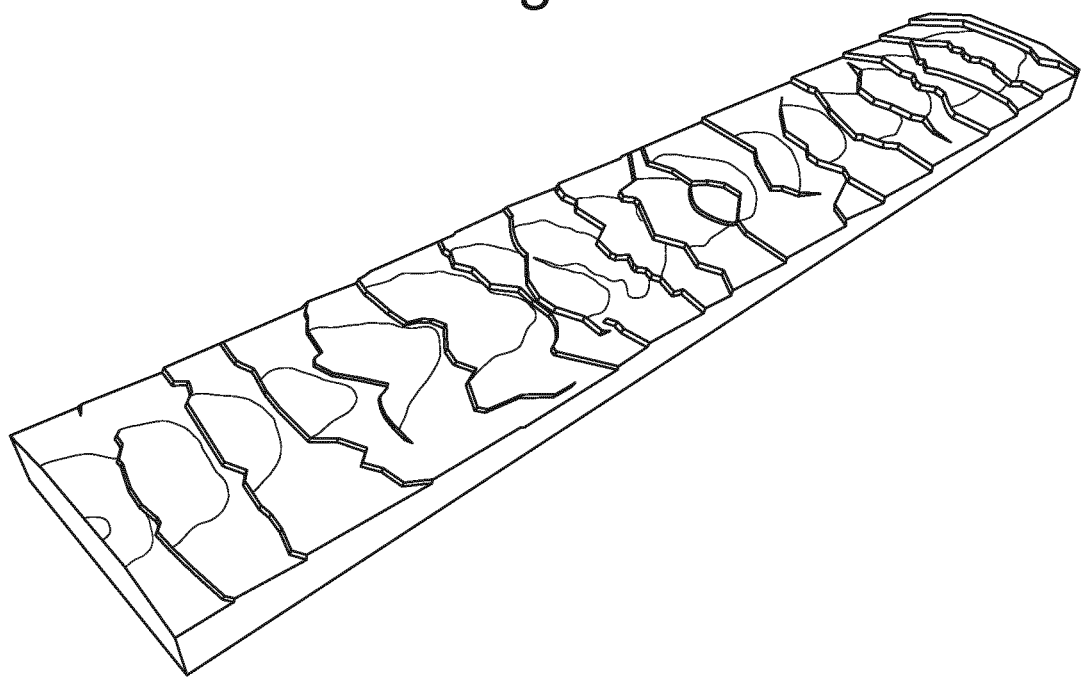
FIG. 1 is a 3D printed object of an untreated hair fibre.

Many assaults occur during everyday life or as part of a normal hair care regime or consumer habit.

Assaults are preferably selected from mechanical assaults, chemical assaults, environmental assaults and mixtures thereof.

Preferred mechanical assaults are combing, brushing, the application of hot irons for curling, straightening or setting and blow drying.

Preferred chemical assaults are treatments that contain chemicals that modify the hair, for example colouring treatments, bleaching, straightening treatments, relaxing treatments and use of surfactants, for example use of shampoo.

Preferred environmental assaults include, for example, humidity, pollution, hard water, salt water, ultra violet light, wind and temperature extremes.

The Image

Preferably, the image is a topographic surface image; more preferably, the topographic surface image is produced using a 3D optical profiler, such as a Sensofar S neox, or laser profilometer.

The topographic surface is converted into a format suitable for a 3D printer, preferably it is exported in a digital file as spatial coordinates (X, Y, Z) of each point which describes the topographic (3D) surface. Preferably, this is completed using a profilometer. An example of a suitable profilometer is the Sensofar S neox profilometer that can produce a 3d image of the surface to be studied. The profilometer software, for example sensoSCAN v5, can export a file ".dat" that is a list of all the X, Y, Z coordinates of each point.

Preferably, the magnified 3D image has a magnification of from 100 to 50,000, preferably 30,000 times.

If desired the conversion of the imaging data iv) comprises a magnification process. The magnification is preferably achieved by change of resolution, units and/or rescale of coordinate axis, producing a new digital file with the new spatial coordinates. A preferred way of magnifying the data points is using Matlab. In this preferred method the ".dat" file is imported in Matlab as a matrix and a set of Matlab scripts are used to manipulate the matrix and change the resolution/scale. It is highly preferred if the matrix is exported into a new ASCII file ".XYZ" as a list of all the X, Y, Z coordinates of each point.

The imaging data is converted into an image suitable for a 3D printer. Preferably, the file is imported in a 3D-CAD software and the 3D surface is applied onto a face of a parallelogram to obtain a 3D object. The resulting 3D image is exported to a digital file compatible with the 3D-printer device software. The XYZ file is preferably imported into a software conversion package, for example the "Rhino" software package, which can convert it into a 3d file and export as a .STL file.

The 3D image is printed to form a 3D object. This can be achieved by using any of the modern 3D printers available, an example is EOS (Electro Optical Systems) EOSINT P380 Selective Laser Sintering printer and a 3D replica of the magnified surface produced.

Preferably, a colour rinse is applied to the 3D model to highlight the areas of interest. The colours can be varied according to the surface height. This is useful in showing up extent of cuticle lift and depth of holes, etc.

The Hair

The method of the invention can be carried out on a single hair fibre, or a bundle of hair fibres.

The hair is preferably human hair.

Beneficial Treatments and Regimes

Preferred treatments and regimes are those that reduce or alleviate the effects of damage to the hair.

Preferred treatments for hair (step vi) are rinse off and leave on products. Preferred hair treatment compositions are selected from a shampoo, a rinse-off hair conditioner, a hair mask, a leave-on conditioner composition, and a pre-treatment composition, more preferably selected from a rinse-off hair conditioner, a hair mask, a leave-on conditioner composition, and a pre-treatment composition, for example an oil treatment, and most preferably selected from a rinse-off hair conditioner, a hair mask and a leave-on conditioner composition.

Rinse off conditioners for use in the invention are conditioners that are typically left on wet hair for 1 to 2 minutes before being rinsed off.

Hair masks for use in the present invention are treatments that are typically left on the hair for 3 to 10 minutes, preferably from 3 to 5 minutes, more preferably 4 to 5 minutes, before being rinsed off.

Leave-on conditioners for use in the invention are typically applied to the hair and left on the hair for more than 10 minutes, and preferably are applied to the hair after washing and not rinsed out until the next wash.

Treatments compositions for use in the method of the current invention preferably comprise conditioning agents. Conditioning agents are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula

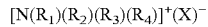

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present invention are monoalkyl quarternary ammonium compounds in which the akyl chain lengthy is $C_8$ to $C_{14}$.

Suitable examples of such materials correspond to the formula

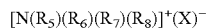

in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions for use in the method of the invention include:

(i) Lauryl trimethylammonium chloride (available commercially as Arquad C35 ex Akzo); cocodimethyl benzyl ammonium chloride (available commercially as Arquad DMCB-80 ex-Akzo)

(ii) Compounds of the formula:

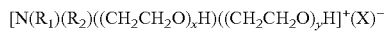

wherein:

x+y is an integer from 2 to 20;

$R_1$ is a hydrocarbyl chain having 8 to 14, preferably 12 to 14, most preferably 12 carbon atoms and containing ether, ester, amido or amino moieties present as substituent's or as linkages in the radical chain;

$R_2$ is a $C_1$-$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

(iii) Compounds of the formula:

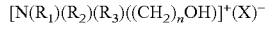

wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$-$C_3$ alkyl groups, and are preferably methyl, and X— is a salt-forming anion such as those selected from halogen, (e.g. chloride, bromide), acetate, citrate, lactate, glycolate, phosphate nitrate, sulphate, alkylsulphate radicals. Suitable examples are lauryldimethylhydroxyethylammonium chloride (available commercially as Prapagen HY ex-Clariant).

Mixtures of any of the foregoing cationic surfactants compounds may also be suitable.

Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 wt. % of the total composition.

A preferred conditioner comprises a conditioning gel phase. Such conditioners and methods for making them are described in WO2014/016354, WO2014/016353, WO2012/016352 and WO2014/016351.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present invention may preferably comprise a miscellar structured liquid.

The pH of a conditioner comprising the present composition is preferably 3-5. More preferably the pH of the composition is 4.5-5.5.

Where the composition has a pH of less than 3.10 it is preferred that it is in the form of a conditioning mask for intense treatment.

Further conditioning ingredients include conditioning oils, preferably selected from coconut oil and olive oil.

The invention will now be illustrated by the following non-limiting Examples:

EXAMPLES

Specimen hair fibres were sampled from a human head and the untreated specimens were imaged according to the method below. The fibres were then treated with bleach and imaged as before.

The method of treating with bleach was as follows:
Commercially available in-homes bleach products, L'Oreal Platine Precision Powder Bleach and Excel Crème Peroxide (9% Vol) were used.

The hair was dark brown European hair, in 7 g/10" Flat Metal switches.

Bleach powder (60 g) and crème peroxide (120 g) were placed in a tinting bowl and mixed to a smooth, creamy consistency.

A switch of hair was spread (in a fan shape) on a sheet of aluminum foil.

The freshly prepared bleach mixture was applied to the hair with a tinting brush, ensuring even coverage on each side.

The switch was then wrapped in the aluminum foil and left to develop at ambient temperature for 30 minutes. The switch was then removed from the foil and rinsed for 2 minutes under the tap, running the fingers down the switch to ensure complete removal of the bleach.

Switches were subjected to the bleaching treatment 4 or 8 times in order to show the effect of repeated bleaching assaults.

Imaging Method

The topographic surface of the hair fibres was converted into a format suitable for a 3D printer, by exporting in a digital file as spatial coordinates (X, Y, Z) of each point which describes the topographic (3D) surface using a sensoSCAN v5 with a Sensofar S neox profilometer.

The resulting digital file data was magnified by importing to Matlab as a matrix and using Matlab scripts to manipulate the matrix and change the resolution/scale. The matrix was then exported into a new ASCII file ".XYZ" as a list of all the X, Y, Z coordinates of each point. The magnification was 30,000 times.

The imaging data was converted into an image suitable for a 3D printer using 3D-CAD software and the 3D surface was applied onto a face of a parallelogram to obtain a 3D object. The resulting 3D image was exported to a digital file compatible with the 3D-printer device software by use of the "Rhino" software package, which converted it into a 3D file and exported it as a .STL file.

The 3D image was then printed to form a 3D object. This was achieved by using an EOS (Electro Optical Systems) EOSINT P380 Selective Laser Sintering printer and a 3D replica of the magnified surface produced.

Comparing and analysing the resulting 3D images demonstrated the effect of the bleach assault on the hair.

Figure 2:
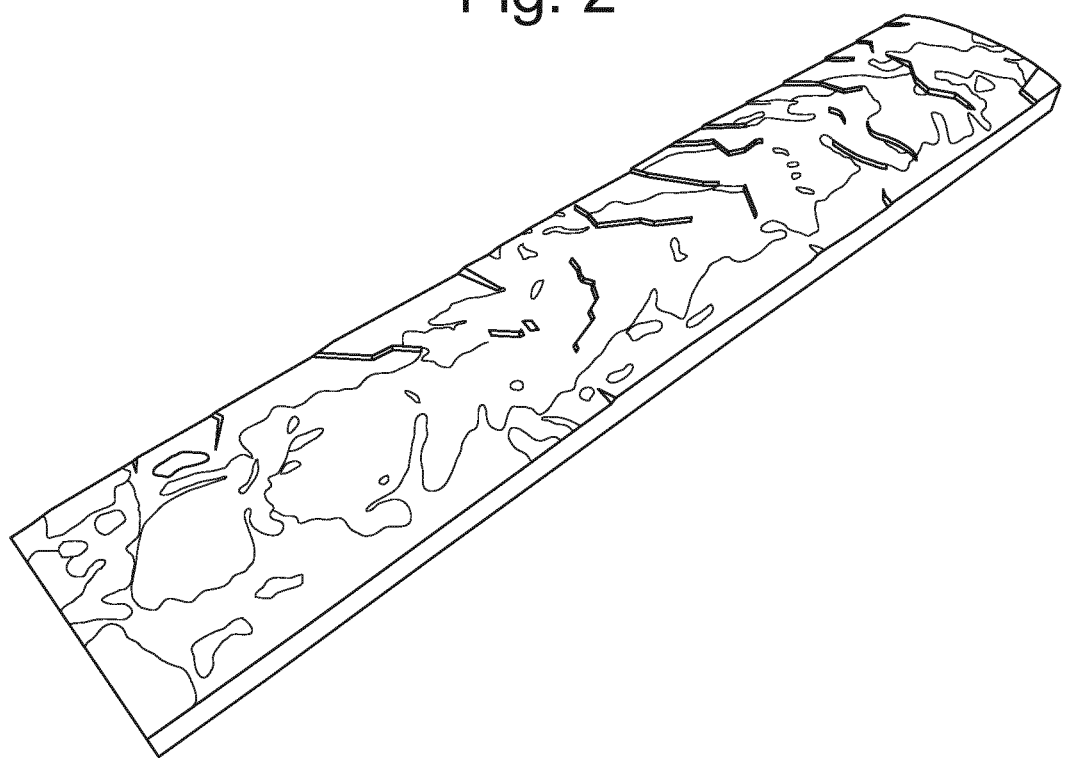
FIG. 2 is a 3D printed object of a hair fibre that has been treated.
Figure 3:
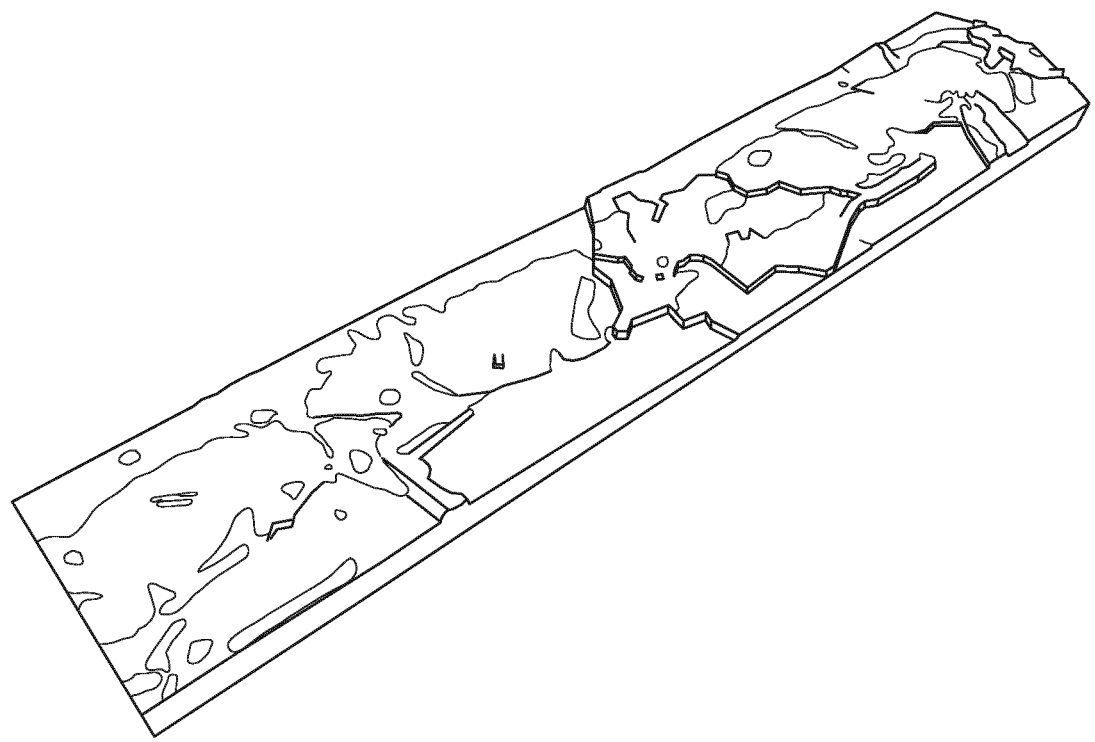
FIG. 3 is a 3D printed object of another hair fibre that has been treated.

The results are shown in FIGS. 1, 2 and 3, where:
FIG. 1 is a 3D printed object of an untreated hair fibre.
FIG. 2 is a 3D printed object of a hair fibre that has been treated 4 times with bleach.
FIG. 3 is a 3D printed object that has been treated 8 times with bleach.

It is possible to see positive and negative depth of surface features of the hair fibres, and to handle the objects such that all aspects may be closely examined in detail, both visually and tactilely. The effect of the bleaching assault is clear, where cuticle erosion and aspects of damage to the outer structure of the hair surfaces is apparent.

The invention claimed is:

1. A method of analysing at least one hair surface using a 3D printer, the method comprising:
    collecting a first imaging data for the at least one hair surface,
    applying at least one assault to the at least one hair surface,
    collecting a second imaging data for the at least one hair surface after applying the at least one assault,
    converting the first imaging data into a first formatted data, the first formatted data associated with the 3D printer,
    converting the second imaging data into a second formatted data, the second formatted data associated with the 3D printer,
    producing a first 3D model of the at least one hair surface from the 3D printer using the first formatted data,
    producing a second 3D model of the at least one hair surface from the 3D printer using the second formatted data;
    comparing the second 3D model to the first 3D model, and
    assessing a first degree of damage to the at least one hair surface based on the comparison of the second 3D model to the first 3D model.

2. The method of claim 1, further comprising, after assessing the first degree of damage to the at least one hair surface:
    applying at least one assault to the at least one hair surface,
    collecting a third imaging data for the at least one hair surface,
    converting the third imaging data into a third formatted data, the third formatted data associated with the 3D printer,
    producing a third 3D model of the at least one hair surface from the 3D printer using the third formatted data;
    comparing the third 3D model to the first 3D model, and
    assessing a second degree of damage to the at least one hair surface based on the comparison of the third 3D model to the first 3D model.

3. The method of claim 1, further comprising, before comparing the second 3D model to the first 3D model:
    determining a first area of interest on the first 3D model;
    applying a first colour rinse to the first area of interest;
    determining a second area of interest on the second 3D model; and
    applying a second colour rinse to the second area of interest.

4. The method of claim 1, wherein converting the first imaging data into the first formatted data comprises magnifying the first imaging data 30,000 times; and
    wherein converting the second imaging data into the second formatted data comprises magnifying the second imaging data 30,000 times.

5. A method of analysing at least one hair surface using a 3D printer, the method comprising:
    collecting a first imaging data for the at least one hair surface,
    converting the first imaging data into a first formatted data associated with the 3D printer,
    producing a first 3D model of the at least one hair surface from the 3D printer using the first formatted data,
    analysing the first 3D model to determine a first set of properties of the at least one hair surface,
    assessing a first degree of damage to the at least one hair surface based on the first set of properties,
    selecting a first treatment based on at least one of the first set of properties or the first degree of damage;
    applying the first treatment to the at least one hair surface,
    collecting a second imaging data for the at least one hair surface after the first treatment has been applied,
    converting the second imaging data into a second formatted data, the second formatted data associated with the 3D printer,
    producing a second 3D model of the at least one hair surface from the 3D printer using the second formatted data,
    comparing the second 3D model to the first 3D model, and
    assessing a first degree of beneficial effect to the at least one hair surface based on the comparison of the second 3D model to the first 3D model.

6. The method of claim 5, further comprising, after collecting the first imaging data:
    applying at least one assault to the at least one hair surface; and
    collecting a third imaging data for the at least one hair surface after applying the at least one assault.

7. The method of claim 5, further comprising, after assessing the first degree of beneficial effect:
    applying the first treatment to the at least one hair surface,
    collecting a third imaging data for the at least one hair surface after the first treatment has been applied,
    converting the third imaging data into a third formatted data, the third formatted data associated with the 3D printer,
    producing a third 3D model of the at least one hair surface from the 3D printer using the third formatted data,
    comparing the third 3D model to the first 3D model, and
    assessing a second degree of beneficial effect to the at least one hair surface based on the comparison of the third 3D model to the first 3D model.

8. The method of claim 5, wherein the first degree of damage is assessed by comparing the first set of properties to a scale set of properties.

9. The method of claim 5, wherein the first treatment comprises application of a hair treatment composition to the at least one hair surface.

10. The method of claim 9, wherein the hair composition is at least one of a rinse-off hair conditioner, a hair mask, a leave-on conditioner composition, or a pre-treatment composition.

* * * * *